(12) United States Patent
Kosegarten

(10) Patent No.: US 9,579,481 B2
(45) Date of Patent: Feb. 28, 2017

(54) DEVICE AND METHOD FOR DEPLETING ACIDIC GASES FROM GAS MIXTURES

(75) Inventor: Annette Kosegarten, Krummesse (DE)

(73) Assignee: Drägerwerk Safety AG & Co. KGaA (DE)

( * ) Notice: Subject to any disclaimer, the term of this patent is extended or adjusted under 35 U.S.C. 154(b) by 516 days.

(21) Appl. No.: 13/814,978

(22) PCT Filed: Aug. 11, 2011

(86) PCT No.: PCT/EP2011/004045
§ 371 (c)(1),
(2), (4) Date: Apr. 12, 2013

(87) PCT Pub. No.: WO2012/019770
PCT Pub. Date: Feb. 16, 2012

(65) Prior Publication Data
US 2013/0213396 A1    Aug. 22, 2013

(30) Foreign Application Priority Data

Aug. 11, 2010 (EP) .................................. 10008378

(51) Int. Cl.
*A61M 16/22* (2006.01)
*A62B 19/00* (2006.01)
(Continued)

(52) U.S. Cl.
CPC .............. *A61M 16/22* (2013.01); *A62B 19/00* (2013.01); *B01D 53/02* (2013.01); *B01D 53/62* (2013.01);
(Continued)

(58) Field of Classification Search
CPC ........ A01N 25/18; A01N 25/34; A01N 59/00; A23L 3/34; A23L 3/3436; A23L 3/3454; A23L 3/3463; A23L 3/3508; A23L 3/358; A61L 2/20; A61L 9/014; A61L 9/145; A61M 16/00; A61M 16/009; A61M 16/0093; A61M 16/01; A61M 16/0808; A61M 16/10; A61M 16/104; A61M 16/16; A61M 16/161; A61M 16/18; A61M 16/22; A62B 19/00; A62B 21/00;A62B 23/00; A62B 23/02; A62B 7/00; A62B 7/02; A62B 7/08; A62B 7/10; A62B 9/00; A62B 9/003; A62D 9/00; B01D 15/00; B01D 17/10; B01D 27/08; B01D 29/00; B01D 36/00; B01D 36/003; B01D 47/02; B01D 47/021; B01D 47/04; B01D 53/02; B01D 53/025; B01D 53/04; B01D 53/0415; B01D 53/14; B01D 53/26; B01D 53/261; B01D 53/62; B01D 53/68; B01J 20/0229; B01J 20/0281; B01J 20/04; B01J 20/041; B01J 20/043; B01J 20/103; B01J 20/106; B01J 20/16; B01J 20/165; B01J 20/18; B01J 20/223; B01J 20/261; B01J 20/267; B01J 20/28033; B01J 20/28035; B01J 20/2804; B01J 20/2805; B01J 20/3092; B63C 11/02; B63C 11/18; B63C 11/24; B65D 81/26; B65D 81/268; C10M 175/005; F24F 3/16; F28B 9/00; G21F 9/00; G21F 9/02
(Continued)

(56) References Cited

U.S. PATENT DOCUMENTS 2,403,413 A * 7/1946 Thurman ................ C11D 13/04
                                                        252/367.1
4,193,966 A * 3/1980 Dowgul ................. A62B 19/00
                                                        128/205.28
(Continued)

FOREIGN PATENT DOCUMENTS

EP          0 939 671 B1    9/1999
WO          WO 98/23370     6/1998

OTHER PUBLICATIONS

The United States Pharmacopeia USP 27, NJ 22; The National Formulary; by authority of the United States Pharmacopeial Convention, Inc., meeting at Washington, D.C., Apr. 12-16, 2000.

*Primary Examiner* — Annette Dixon
(74) *Attorney, Agent, or Firm* — Locke Lord LLP; Alan B. Clement; Peter J. Fallon

(57) ABSTRACT

The invention relates to a device and method for depleting acidic gases, in particular $CO_2$, from gas mixtures, in
(Continued)

particular respiratory gas, using hydroxide compounds and moisture absorbing substances in the form of super-absorbing polymer or vermiculite.

18 Claims, 2 Drawing Sheets

(51) Int. Cl.
*B01D 53/02* (2006.01)
*B01D 53/62* (2006.01)

(52) U.S. Cl.
CPC ..... *B01D 2251/40* (2013.01); *B01D 2253/202* (2013.01); *B01D 2257/504* (2013.01); *B01D 2259/4533* (2013.01); *Y02C 10/04* (2013.01); *Y02C 10/08* (2013.01)

(58) Field of Classification Search
USPC ............ 128/200.24, 200.29, 201.25, 201.26, 128/201.27, 202.26, 202.27, 203.12, 128/203.16, 203.21, 204.13, 204.15, 128/204.16, 204.17, 204.18, 204.22, 128/204.26, 205.11, 205.12, 205.22, 128/205.24, 205.2, 205, 28, 206.17, 128/907, 909; 55/421, 482, 486, 487, 498, 55/512, 518, DIG. 33, DIG. 35; 95/114, 95/115, 139, 150, 226; 96/108, 111, 113, 126, 132, 135, 96/137, 152, 290, 329
See application file for complete search history.

(56) References Cited

U.S. PATENT DOCUMENTS

| | | | |
|---|---|---|---|
| 4,492,649 A | | 1/1985 | Cheh et al. |
| 4,790,327 A | * | 12/1988 | Despotis ........... A61M 16/0488 128/205.23 |
| 4,826,805 A | * | 5/1989 | Fukunaga et al. .............. 96/135 |
| 5,487,380 A | * | 1/1996 | Grabenkort .............. 128/204.15 |
| 5,577,494 A | * | 11/1996 | Kuypers et al. ......... 128/201.13 |
| 6,279,571 B1 | * | 8/2001 | Meckes .................. A62B 17/04 128/201.22 |
| 8,596,272 B2 | * | 12/2013 | Koulechov et al. ..... 128/205.27 |
| 2004/0126316 A1 | * | 7/2004 | Peterson ................. C01B 31/18 423/648.1 |
| 2005/0235830 A1 | * | 10/2005 | Hughes ............................ 96/108 |
| 2008/0092890 A1 | * | 4/2008 | Shahaf ..................... 128/204.15 |
| 2008/0271603 A1 | * | 11/2008 | Triplett et al. .................. 95/150 |
| 2009/0035199 A1 | * | 2/2009 | Mortson .............. B01D 53/526 423/224 |
| 2009/0169461 A1 | * | 7/2009 | Miyake .............. B01D 53/1475 423/419.1 |

* cited by examiner

DEVICE AND METHOD FOR DEPLETING ACIDIC GASES FROM GAS MIXTURES

CROSS REFERENCES TO RELATED APPLICATIONS

This application is a National Stage patent application of International Patent Application Number, PCT/EP2011/004045, filed on Aug. 11, 2011, which claims priority to German Patent Application No. DE 10 008 378.1, filed on Aug. 11, 2010.

BACKGROUND OF THE INVENTION

The invention relates to an apparatus and a method for depleting $CO_2$, from breathing gas using hydroxide compounds and moisture-absorbing substances.

Closed and semi-closed breathing circuits serve to allow the user breathing wholly or partially independent from ambient air. This is true, for example, for circuit breathing apparatuses of firefighters, for mines, but also for escape devices, diving equipment or submarines. By circulating the respiratory air breathing gas can be saved. This is particularly important for use in anesthesia. It is necessary, however, to deplete carbon dioxide produced and exhaled by the user.

Depleting carbon dioxide is generally accomplished by alkali or alkaline earth metal hydroxides with a variety of additives. For example, according to the following reaction schemes:

$$CO2+H_2O \rightarrow H_2CO_3$$

$$H_2CO_3+2NaOH \rightarrow Na_2CO_3+2H_2O$$

$$Na_2CO_3+Ca(OH)_2 \rightarrow CaCO_3+2NaOH$$

$$Ca(OH)_2+CO_2 \rightarrow CaCO_3+H_2O+\text{heat AHR}=-113 \text{ kJ/mol}$$

Alkaline earth metal hydroxides used in such a manner are often referred to soda lime. Besides alkaline earth metal hydroxides, water is reactant, which is needed for optimum reactivity of the $CO_2$ absorber.

For use in anesthesia already several absorption materials have been proposed. Known absorption materials are often alkaline earth metal chlorides (EP 0939671 B1, WO 98/23370), simple silicates or also alkaline earth metal sulfates (EP 0939671 B1). For the purposes of the present invention, it is necessary to achieve a higher absorption capacity for carbon dioxide, in particular when using moist gases.

It has been discovered that the addition of conventional humectants can lead to losses in the absorption capacity for acid gases of the absorber, and to a reduction in abrasion resistance.

When storing soda lime, water can be lost through the packaging. This may decrease the $CO_2$ absorption capacity, because water is no longer available as reactant in sufficient quantity (see reaction schemes above). Additionally, during transportation in the respective packaging there may be abrasion (dust) of the soda lime. This dust is undesirable as it will be, without appropriate countermeasures, present in the breathing circuit and included therein.

The object of the invention is to provide absorption material for acid gases, without the disadvantages of the prior art and, in particular, on the one hand, providing water and, on the other hand, binding water, and being storage-stable, i.e., the absorption performance of the absorber over the storage period is maintained, without loss of $CO_2$ absorption capacity. A simultaneous increase in abrasion resistance is also desirable.

This object is achieved by the subject matter of the independent claims. Preferred embodiments are subject of the dependent claims, or are described below.

BRIEF SUMMARY OF THE INVENTION

The subject matter of the invention is the simultaneous use of at least one hydroxide compound as an absorber for the acid gas of a gas mixture, and at least one water-absorbing substance in the form of a superabsorbent polymer (SAP) and/or vermiculite, said hydroxide compound and water-absorbing substance in the form of a superabsorbent polymer and/or vermiculite being in immediate spatial contact with each other. The acid gas is in particular carbon dioxide ($CO_2$). The gas mixture comprises breathing gas, such as provided by a exhaling process. Such exhaled breathing gas has residual moisture and is warmed up.

BRIEF DESCRIPTION OF THE SEVERAL VIEWS OF THE DRAWING

The invention and their properties, respectively, are described in more detail by the figures.

DETAILED DESCRIPTION OF THE INVENTION

Figure 1:
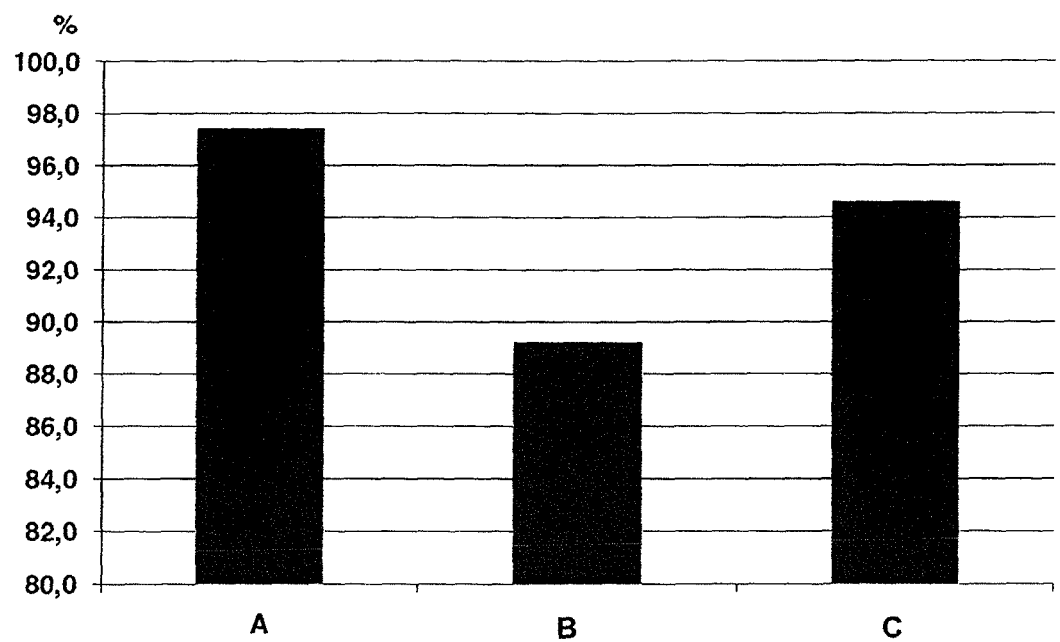
FIG. 1 shows the abrasion tendency of different soda limes.

The gas mixture may also be a diving gas comprising, for example, a mixture of:

a) nitrogen, at a volume fraction of <79% by volume and oxygen, at a volume fraction of >21% by volume.

b) oxygen, nitrogen and helium, e.g., 20 to 40% by volume oxygen, 20 to 40% by volume helium and 30-50% by volume nitrogen.

Suitable hydroxide compounds are, in particular, alkaline earth metal hydroxides together with sodium hydroxide such as calcium hydroxide together with sodium hydroxide and, optionally, lithium hydroxide. Preferably, said alkali hydroxides are used in smaller proportions (by mass) than the alkaline earth metal hydroxides.

The water-absorbing substances, hereinafter referred to also as moisture binding agent, are superabsorbent polymers (SAP) or a vermiculite (layer silicate). These act on the one hand as a humectant and on the other hand, they have a high moisture binding capacity.

Superabsorbent polymers according to the present invention are polymers which are able to absorb an amount of water many times their own weight. Suitable superabsorbent agents are, for example, copolymers of acrylic acid and acrylate salts (e.g., sodium acrylate), prepared using cross-linking agents (e.g. core cross-linker). For the cross-linked polyacrylic acids (cross-linked) different crosslinking agents may be used. Crosslinking the polymer chains renders the polymer insoluble in water. Water penetrates the polymer particles, so that it swells and binds the water. Other superabsorbent polymers include cross-linked polysaccharide derivatives.

Superabsorbent polymers of this invention are understood to be cross-linked organic polymers which can swell but are not soluble in water. They swell with water to many times their own weight. Suitable superabsorbent polymers include, form a chemical perspective, partially neutralized and cross-linked polyacrylic acids, (partial) hydrolysates of starch-acrylonitrile graft copolymers, (partially) neutralized starch acrylic acid graft copolymers, (partially) saponified vinyl acetate-acrylic acid ester copolymers, (partially) hydrolyzed acrylonitrile or acrylamide copolymers, cross-linked products of such hydrolysates and polymers of cross-linked cationic monomers. In particular, the following monomers may be contained alone or in combination in the cross-linked superabsorbent polymers: acrylic acid, methacrylic acid, vinylsulfonic acid, styrenesulfonic acid, 2-(meth)acrylamide-2-methylpropane sulfonic acid, 2-(meth)acryloylethanesulfonic acid, 2-(meth)acryloylpropanesulfonic acid, and the salts of the abovementioned acids. Further (meth) acrylamide, N-ethyl (meth)acrylates, N,N-dimethylaminopropyl (meth)acrylates, N,N-dimethylaminopropyl (meth) acrylamides and their quaternary salts, and vinylpyrrolidone. Suitable crosslinking agents are, for example, ally! methacrylate, diethylene glycol diacrylate, ethoxylated trimethylolpropane triacrylate, ethylene glycol diglycidyl ether, methylenebisacrylamide, tetraallyloxyethane, triallylamine and trimethylolpropane triacrylate. For more information on superabsorbers, see the book "Modern Superabsorbent Polymer Technology", published by Fredric L. Buchholz and Andrew T. Graham, Wiley-VCH (1998).

Preferred are superabsorbent polymers based on polyacrylate, polymethacrylate, and the corresponding copolymers.

Vermiculite is a layered silicate and can be represented by the general composition: $(Mgo.5, Ca0.5, Na, K)0.7(Mg, Fe, Al)3[(OH)21(Al, S02Si2010] \times 4H_2 0$.

Super absorbers, depending on the formulation, take up water up to 1000 times their own weight. Vermiculite still up to 20 times, while conventional humectants such as calcium chloride, can take up moisture only about twice its own weight.

The absorber including the absorber material, based on the absorber, contains more than 10% by weight, more preferred more than 15% by weight, and possibly also more than 20% by weight of water. The degree of loading with water in % by weight can be determined, for example, by means of the differential value obtained by drying at elevated temperatures.

In conclusion, according to the present invention, an absorber material is understood to be the sum of the hydroxide compounds, superabsorbent polymers and vermiculite. Besides the absorber material, the absorber may contain, in addition, other components.

According to one embodiment, the above water-absorbing substances (superabsorbent polymer(s) and/or vermiculite, but without water) constitute 0.5 to 15% by weight, in particular 0.5 to 5% by weight of the absorber material (100% by weight). Hydroxide compound make up the remainder up to 100%.

The invention is further characterized by the structure of the absorber. In the absorber, the humectant is, e.g. in the form of an absorber bed, in contact with the hydroxide compound, preferably in all-round contact:

All components may be present together in form of a powder or as granules (fill).

Humectant and hydroxide compound each in powder or granular form are arranged in layers next to/on top of each other, which are separated from each other, e.g., by a grid structure such as a nonwoven fabric.

Hydroxide compound and/or water-absorbing substance are applied together, possibly also in layers, on a support material, such as a nonwoven fabric (supported).

In the absorption bed, the humectant is arranged around the hydroxide, for example, by the hydroxide compound being present as granules and the water-absorbing substance, in particular, the polymeric super absorber, being applied to the granules, or vice versa.

The hydroxide compound may be present, optionally together with other substances, in the form of granules, typically in the particle size range between 1 to 5 mm. Particle size analysis can be based, for example, on a method according to U.S. Pharmacopoeia 27 NF22. Here, the granular form can be irregular, but also semi-spherical or spherical, or as small rolls or tablet.

The moisture binding agent may also be arranged around the $CO_2$-absorbent as granules, or on a support, wherein the moisture binding agent is a support for the hydroxide compound or vice versa.

It is also possible to process hydroxide compound and moisture binding agent together to form pellets, in order to produce a bulk therefrom, or to load both on solid supports. Such carriers can have a grid, honeycomb or network structure.

The invention is primarily used in circuit breathing apparatuses and in anesthetics, however, it can be used also in any other application in which current absorption materials on the basis of hydroxides are used for carbon dioxide. In this case usually breathing systems are used in which the breathing gas is circulating and is fed back to the breather after removing/depleting the exhaled carbon dioxide. Examples of circuit breathing apparatuses include circuit diving apparatuses, also called "rebreathers". Consumed breathing gas is replaced, where volatile anesthetics are added to anesthesia systems.

Circuit breathing apparatuses can have a closed or semi-closed design. Semi-closed circuit breathing apparatuses are those in which the oxygen consumed is replaced with the aid of a (mixed) gas source. Due to the continuous or consumption-dependent addition of breathing gas into the circuit, there is a need to discharge excess breathing gas by means of a suitable valve, or by breathing through the mask.

Passive semi-closed circuit breathing apparatuses are those in which the oxygen consumed is replaced with the aid of a (mixed) gas source. Here, at every breath, a constant fraction (e.g. 1:5 to 1:20) of the circulating volume is removed from the apparatus and discharged to the outside. The reduced volume is then automatically (by means of valves) refilled with mixed gas.

The benefit of the present invention resides in the fact that due to the moisture binding agent a large amount of water in the absorption material itself may be bound, and thus will be available for reaction mediation with the acid gas and thereby extending the storage period.

In the case of an application in anesthetics it is to be expected that no or reduced anesthetic decomposition will occur, as this is facilitated by drying, and this is prevented by the addition of a moisture binding agent. In addition, less water of reaction from the absorption bed is released into the breathing circuit, so that the operation of the apparatus is less impacted and a physiologically pleasant inhaling moisture may be set. A positive side effect is the fact that the absorber material is consumed anyway after each use and must be replaced, and therefore no additional effort to empty condensate traps or similar is required by the user. Due to the property of the superabsorbent to form hydrogen bonds, which then hold the water, the mechanical strength increases also, since especially in connection with water the cross-linking within the absorber is increased.

Not every water binding agent exhibits the above advantages, as demonstrated by the following examples Formulation Example 1

Calcium hydroxide was mixed with 3% by weight of sodium hydroxide and 1% by weight of acrylate-based superabsorbent and an excess of water. Then, the paste is granulated and dried to a water content of about 16%. The resulting product is shown in FIGS. 1 and 2 as product A.

Figure 2:
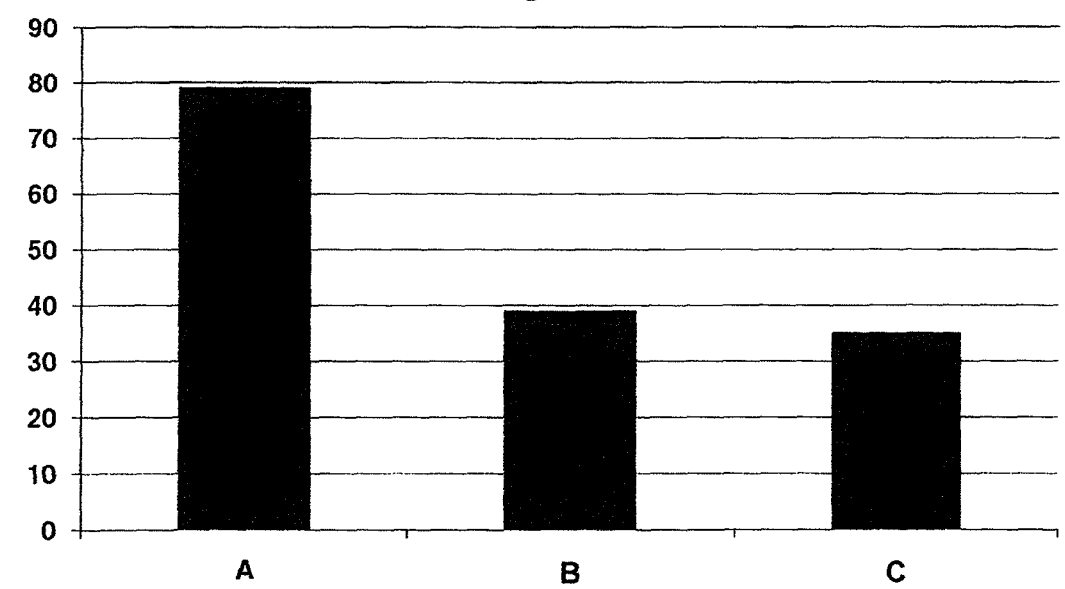
FIG. 2 shows the $CO_2$ absorption capacity of different soda limes.

The abrasion resistance was determined in a friabilator, as it is used, inter alia, for tablet testing, over 7 h, and is shown in FIG. 1. A conventional $CO_2$ absorber B contains calcium chloride as a moisture binding agent, another conventional product C contains silicates.

In the case of product B, and C, the abrasion resistance is reduced. Both soda limes with binding agents show a reduction in $CO_2$ performance in the STANAG 1411 $CO_2$ test (see FIG. 2). When using super absorbers, the abrasion resistance is increased with good $CO_2$ performances.

The abrasion test was carried out so that 10 g of dust-free $CO_2$-absorber rotated 7 hours in a friabilator, followed by passing through a 0.42 mm screen. 100 minus the percentage abrasion calculated (<0.42 mm) gave the abrasion resistance. The $CO_2$ absorption test is described in NATO standard 1411.

Figure 3:
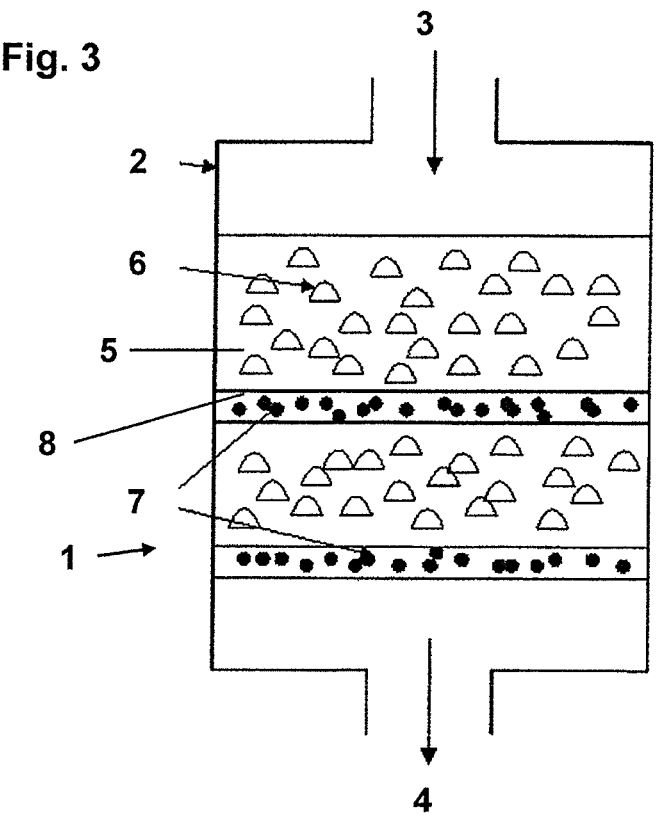
FIG. 3 shows a possible arrangement in a filter cartridge.
Figure 4:
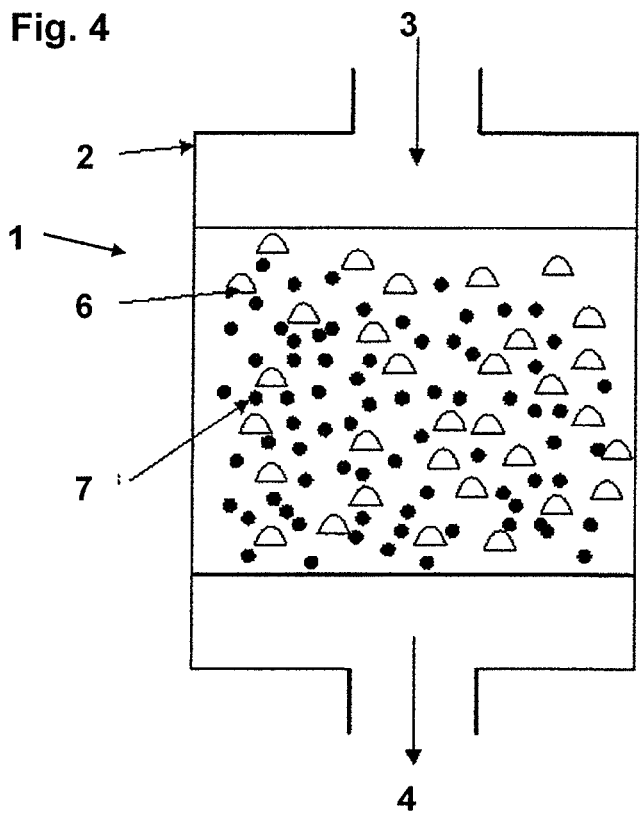
FIG. 4 shows another possible arrangement in a filter cartridge.

FIG. 4 shows schematically the structure of a $CO_2$ absorber in the form of a filter element, such as may be used in a respiratory system. $CO_2$ filter element 1 has a housing 2 having a gas inlet 3 and a gas outlet 4 with an absorber designed as absorber bed 5, provided with $CO_2$ absorber 6 and moisture binding agent 7 in form of a fill. FIG. 3 shows a structure of the absorber in layers, which are separated by a nonwoven fabric 8.

The invention claimed is:

1. A closed or semi-closed circuit breathing apparatus for depleting carbon dioxide from a gas mixture, the breathing apparatus comprising
an absorber which contains as absorber material:
carbon dioxide-absorbing substances, comprising at least one hydroxide compound comprising at least sodium hydroxide and at least an alkaline earth metal hydroxide; and
water-absorbing substances, comprising a superabsorbent polymer (SAP) or vermiculite or both, wherein
hydroxide compound(s) and superabsorbent polymer (SAP); or
hydroxide compound(s) and vermiculite; or
hydroxide compound(s) and superabsorbent polymer (SAP) and vermiculite form the absorber material,
wherein water-absorbing substances and hydroxide compound(s) are each directly in contact with each other,
wherein the gas mixture is breathing gas provided by an exhaling process being part of a breathing process, and the absorber is flown through by the breathing gas,
wherein the absorber independently:
a) has a layer structure comprising at least three different layers of the absorber material, wherein at least one layer is surrounded at least partially by two more other layers and the carbon dioxide-absorbing substances and the water-absorbing substances are present in the form of a powder or granules;
b) is a mixed fill of particles comprising the absorber material and the carbon dioxide-absorbing substances and the water-absorbing substances are present in the form of a powder or granules;
c) the superabsorbent polymer and the hydroxide compound or
the vermiculite and the hydroxide compound or
the superabsorbent polymer and the vermiculite and the hydroxide compound are applied to a support;
d) the superabsorbent polymer or the vermiculite or both are applied to the hydroxide compound as a carrier, or vice versa; or
e) the hydroxide compound and superabsorbent polymer or
the hydroxide compound and the vermiculite or
the hydroxide compound and the superabsorbent polymer and the vermiculite are each jointly incorporated into particles and the carbon dioxide-absorbing substances and the water-absorbing substances are present in the form of a powder or granules.

2. The circuit breathing apparatus according to claim 1, wherein the carbon dioxide-absorbing substances comprises sodium hydroxide and calcium hydroxide.

3. The circuit breathing apparatus according to claim 1, wherein the hydroxide compounds comprise an alkaline earth metal hydroxide and an alkali hydroxide.

4. The circuit breathing apparatus according to claim 3, wherein the amount of alkali hydroxide is from 0.5% to 8% by weight, based on the mass of the hydroxide compounds used.

5. The circuit breathing apparatus according to claim 1, wherein the hydroxide compound further comprises lithium hydroxide.

6. The circuit breathing apparatus according to claim 1, wherein the water-absorbing substances constitute 0.5% to 15% by weight of the absorber material, excluding any absorbed water.

7. The circuit breathing apparatus according to claim 1, wherein the absorber contains more than 10% by weight of water.

8. The circuit breathing apparatus according to claim 1, wherein the breathing gas is anesthesia breathing gas comprising volatile anesthetics, or a diving gas.

9. The circuit breathing apparatus according to claim 1, wherein the absorber is part of a replaceable cartridge or refillable cartridge or a replaceable and refillable cartridge.

10. The circuit breathing apparatus according to claim 1, wherein the absorber contains more than 15% by weight of water.

11. The circuit breathing apparatus according to claim 1, wherein the absorber contains more than 20% by weight of water.

12. A process for removing carbon dioxide from a gas mixture using the circuit breathing apparatus according claim 1.

13. A use of an absorber comprising as an absorber material:
carbon dioxide-absorbing substances, including at least one hydroxide compound comprising at least sodium hydroxide and at least an alkaline earth metal hydroxide; and water-absorbing substances, comprising a superabsorbent polymer (SAP) or vermiculite or both, wherein the hydroxide compound(s) and the superabsorbent polymer (SAP); or the hydroxide compound(s) and the vermiculite; or the hydroxide compound(s) and the superabsorbent polymer (SAP) and the vermiculite, wherein the water-absorbing substances and the hydroxide compound(s) are each directly in contact with each other, for removing carbon dioxide from a breathing gas as provided by an exhaling process, wherein the breathing gas flows through the absorber in a closed or semi-closed circuit breathing apparatus, is circulated and is adapted to be fed back to the breather after removing/depleting the exhaled carbon dioxide, wherein the absorber independently a) has a layer structure comprising at least three different layers of the absorber material, wherein at least one layer is surrounded at least partially by two more other layers and the carbon dioxide-absorbing substances and the water-absorbing substances are present in the form of a powder or granules;

b) is a mixed fill of particles comprising the absorber material and the carbon dioxide-absorbing substances and the water-absorbing substances are present in the form of a powder or granules;

c) the superabsorbent polymer and the hydroxide compound, or the vermiculite and the hydroxide compound, or the superabsorbent polymer and the vermiculite and the hydroxide compound are applied to a support;

d) the superabsorbent polymer or the vermiculite or both are applied to the hydroxide compound as a carrier, or vice versa; or e) the hydroxide compound and the superabsorbent polymer or the hydroxide compound and the vermiculite or the hydroxide compound and the superabsorbent polymer and the vermiculite are each jointly incorporated into particles and the carbon dioxide-absorbing substances and the water-absorbing substances are present in the form of a powder or granules.

14. The use according to claim 13, wherein the hydroxide compounds include an alkaline earth metal hydroxide and an alkali hydroxide.

15. The use according to claim 14, wherein the amount of alkali hydroxide is from 0.5% to 8% by weight, based on the mass of the hydroxide compounds used.

16. The use according to claim 13, wherein the water-absorbing substances constitute 0.5% to 15% by weight of the absorber material, excluding any absorbed water.

17. The use according to claim 13, wherein the breathing gas is anesthesia breathing gas comprising volatile anesthetics, or a diving gas.

18. A closed or semi-closed circuit breathing apparatus for depleting carbon dioxide from a gas mixture, the breathing apparatus comprising an absorber which contains as absorber material:

carbon dioxide-absorbing substances, comprising at least one hydroxide compound comprising at least sodium hydroxide; and water-absorbing substances, comprising a superabsorbent polymer (SAP) or vermiculite or both, wherein hydroxide compound(s) and superabsorbent polymer (SAP); or hydroxide compound(s) and vermiculite; or hydroxide compound(s) and superabsorbent polymer (SAP) and vermiculite form the absorber material, wherein water-absorbing substances and hydroxide compound(s) are each directly in contact with each other, wherein the gas mixture is breathing gas provided by an exhaling process being part of a breathing process, and the absorber is flown through by the breathing gas, wherein the absorber independently:

a) has a layer structure comprising at least three different solid layers of the absorber material, wherein at least one layer is surrounded at least partially by two more other layers;

b) is a mixed fill of solid particles comprising the absorber material;

c) the superabsorbent polymer and the hydroxide compound or the vermiculite and the hydroxide compound or the superabsorbent polymer and the vermiculite and the hydroxide compound are applied to a solid or flexible support;

d) the superabsorbent polymer or the vermiculite or both are applied to the hydroxide compound as a solid carrier, or vice versa; or e) the hydroxide compound and superabsorbent polymer or the hydroxide compound and the vermiculite or the hydroxide compound and the superabsorbent polymer and the vermiculite are each jointly incorporated into solid particles, and wherein the carbon dioxide-absorbing substances comprises sodium hydroxide and at least one alkaline earth metal hydroxide and at least the greater part of the breathing gas after the depletion of at least some of the carbon dioxide and optional addition of further components is inhaled as part of the same breathing process.

\* \* \* \* \*